United States Patent
Zano et al.

(12) United States Patent (10) Patent No.: US 11,141,139 B1
Zano et al. (45) Date of Patent: Oct. 12, 2021

(54) DEVICE FOR SAFE STORING AND EXPELLING OF A LIQUID SOLUTION

(71) Applicant: AID GENOMICS LTD, Rehovot (IL)

(72) Inventors: Snir Zano, Omer (IL); Itzhak Mintz, Kibbutz Dvir (IL)

(73) Assignee: AID GENOMICS LTD, Rehovot (IL)

( * ) Notice: Subject to any disclaimer, the term of this patent is extended or adjusted under 35 U.S.C. 154(b) by 0 days.

(21) Appl. No.: 17/146,727

(22) Filed: Jan. 12, 2021

(51) Int. Cl.
*A61B 10/00* (2006.01)
*B01L 3/00* (2006.01)

(52) U.S. Cl.
CPC ............ *A61B 10/0045* (2013.01); *B01L 3/50* (2013.01)

(58) Field of Classification Search
CPC ......... A61B 10/045; A61B 10/00; B01L 3/50; B01L 3/00
USPC .................................................. 600/573, 300
See application file for complete search history.

(56) References Cited

U.S. PATENT DOCUMENTS 5,328,484 A * 7/1994 Somers ............... A61M 5/3202
604/110

FOREIGN PATENT DOCUMENTS

WO   WO 97/44076   * 11/1997 ............ A61M 5/315

OTHER PUBLICATIONS

Melero Redrado, Fernando, WO 97/44096 English Machine Translation, Nov. 1997, obtained on Mar. 10, 2021 with Google Translate, pp. 1-7. (Year: 1997).*

* cited by examiner

*Primary Examiner* — Christine T Mui
(74) *Attorney, Agent, or Firm* — Pearl Cohen Zedek Latzer Baratz LLP (57) ABSTRACT

A device for safe storing and expelling of a liquid solution, including: an annular body having a proximal portion and a distal portion and including a transverse member connected along its circumference to an inner lateral surface of the annular body between the proximal portion and the distal portion of the annular body; and a liquid tight piston fitting tightly and movable within the proximal portion of the annular body, wherein the piston includes one or more longitudinal members longitudinally protruding from the piston into an interior of the proximal portion of the annular body, and wherein each of the one or more longitudinal members includes a sharp end to cut the transverse member of the annular body when the one or more longitudinal members being pushed against the transverse member of the annular body.

13 Claims, 10 Drawing Sheets

DEVICE FOR SAFE STORING AND EXPELLING OF A LIQUID SOLUTION

FIELD OF THE INVENTION

The present invention relates to the field of laboratory equipment and, more particularly, to devices for safe storing and expelling of a liquid solution.

BACKGROUND OF THE INVENTION

Some biological tests may require obtaining a sample of a biological material from a subject, for example using a swab stick. After the sample is obtained, the sample is typically positioned into a test tube. Some biological tests may require exposing the obtained sample to liquid solutions in order to prepare the obtained sample for further analysis. For example, some biological tests may require extraction of macromolecules from the obtained sample, e.g., using lysis buffer solutions. Such liquid solutions typically include hazardous materials and thus need to be treated with extra care. Typically, the obtained sample may be exposed to such liquid solutions only at a laboratory facility. However, this causes delays in obtaining test results, especially when the laboratory facility handles large amounts of biological tests.

SUMMARY OF THE INVENTION

Some embodiments of the present invention provide a device for safe storing and expelling of a liquid solution, the device including: an annular body having a proximal portion and a distal portion and comprising a transverse member connected along its circumference to an inner lateral surface of the annular body between the proximal portion and the distal portion of the annular body; and a liquid-tight piston fitting tightly and movable within the proximal portion of the annular body, the piston comprising one or more longitudinal members longitudinally protruding from the piston into an interior of the proximal portion of the annular body, wherein each of the one or more longitudinal members comprises a sharp end to cut the transverse member of the annular body when the one or more longitudinal members is pushed against the transverse member of the annular body.

In some embodiments, the device is configured to store a liquid solution in a volume defined by the inner lateral surface of the annular body, the transverse member of the annular body, and the piston.

In some embodiments, the device further includes a liquid solution in a volume defined by the inner lateral surface of the annular body, the transverse member of the annular body, and the piston.

In some embodiments, the annular body is connectable at its distal end to an open end of a test tube.

In some embodiments, the distal portion of the annular body is screwable to a proximal portion of a test tube.

In some embodiments, the device is configured to cause at least a part of air contained within the proximal portion of the annular body to escape from the proximal portion of the annular body when the piston is being inserted into the proximal portion of the annular body.

In some embodiments, the annular body comprises one or more longitudinal grooves on the inner lateral surface of the annular body, the one or more longitudinal grooves longitudinally extending from the proximal end of the annular body along a part of the proximal portion of the annular body.

In some embodiments, the piston is movable with respect to the annular body between an initial, non-actuated piston position and a final, actuated piston position, and the piston is releasably lockable with respect to the annular body in the initial, non-actuated piston position.

In some embodiments, the piston is one of lockable and releasably lockable with respect to the annular body in the final, actuated piston position.

In some embodiments, the piston includes: a first liquid-tight annular piston body fitting tightly and movable within the proximal portion of the annular body; a transverse piston portion projecting outwardly from a proximal end of the first annular piston body; and a second annular piston body connected to the transverse piston portion and surrounding the first annular piston body such that a gap is formed between the first annular piston body and the second annular piston body, wherein the gap is configured to receive at least a part of the proximal portion of the annular body.

In some embodiments, the piston is screwable to the proximal portion of the annular body, wherein the proximal portion of the annular body comprises an external thread, and wherein the second annular piston body comprises an internal thread mating with the external thread of the proximal portion of the annular body.

In some embodiments, the device further includes a piston locking annular body connected to the second annular piston body and connectable to the annular body.

In some embodiments, the piston locking annular body is connected to the second annular piston body at multiple connection points configured to withstand torque values that are below a predefined torque threshold and configured to break when subjected to torque values that exceed the predefined torque threshold.

In some embodiments, the annular body comprises lateral protrusions projecting outwardly from an external lateral surface of the annular body, the piston locking annular body comprises mating cuts on its lateral surface, and the cuts and the lateral protrusions are shaped and sized to cause each of the cuts to receive and lock one of the lateral protrusions when the piston locking annular body is being longitudinally pressed with respect to the annular body.

In some embodiments, the second annular piston body comprises teeth longitudinally protruding from a distal end of the second annular piston body, the annular body comprises one or more latches mating with the teeth, and the one or more latches are engageable with the teeth when the piston is tightly screwed to the proximal portion of the annular body to prevent unscrewing of the piston from the proximal portion of the annular body.

In some embodiments, the one or more latches project outwardly from an external lateral surface of the annular body.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Some embodiments of the present invention provide a device for safe storing and expelling of a liquid solution into a test tube. The device may be prefilled with a liquid solution, e.g., such as lysis buffer solution, and may safely store the liquid solution. The device may be connectable to a test tube. For example, the device may be screwable to a proximal portion of the test tube. The device may be connected to the test tube immediately after a biological sample obtained from a subject is received within the test tube. Upon connection of the device to the test tube, the device may be actuated to expel the liquid solution into the test tube. As long as the device is connected to the test tube, the device may prevent outflow of the liquid solution from the test tube.

The test tube with the obtained sample, the liquid solution and the device connected thereto may be safely delivered to a laboratory facility. The liquid solution may interact with the obtained sample during the delivery of the test tube to the laboratory facility so that the obtained sample may be ready for further analysis immediately with its arrival at the laboratory facility.

Figure 1A:
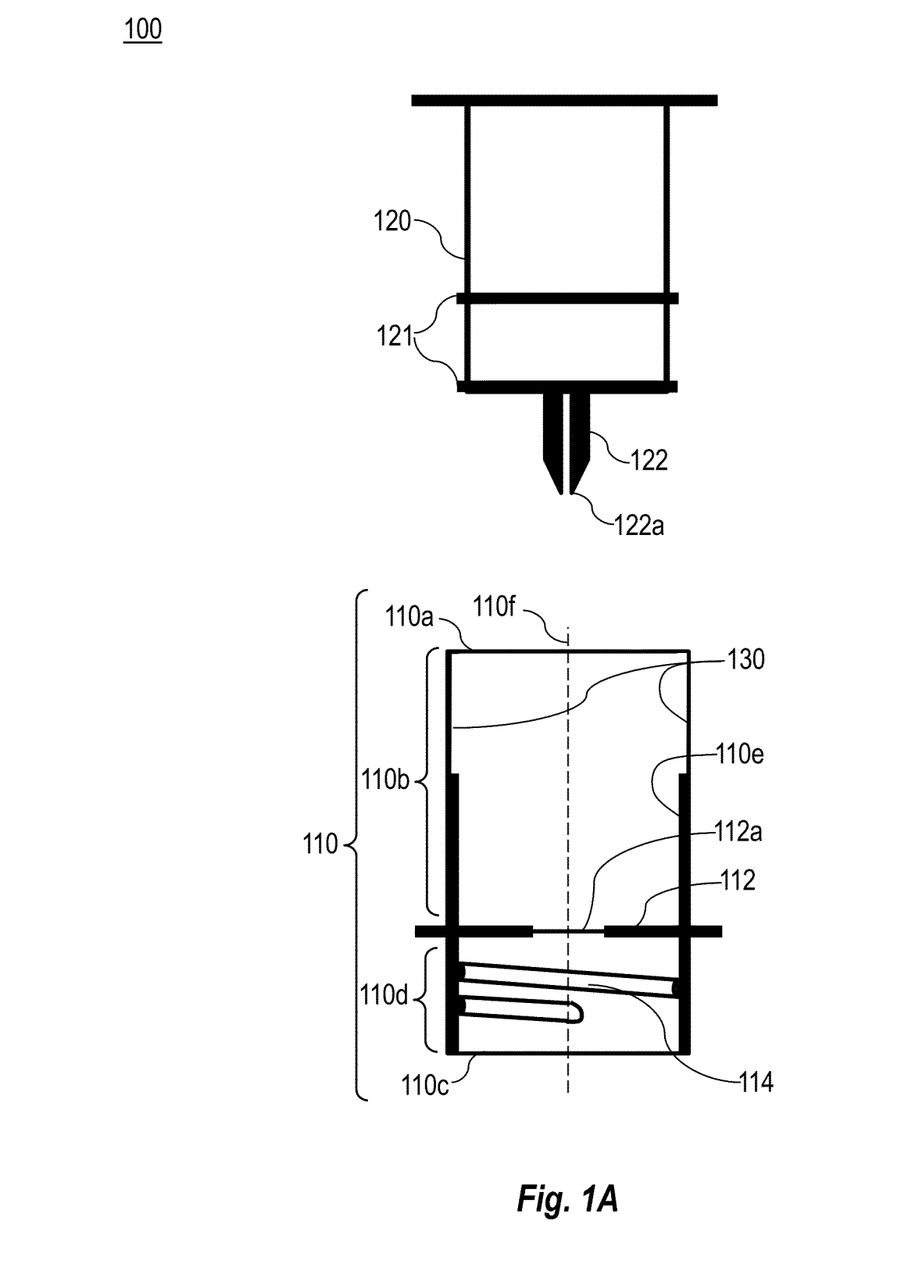
FIG. 1A is a schematic illustration of a device for safe storing and expelling of a liquid solution, according to some embodiments of the invention.

Reference is now made to FIG. 1A, which is a schematic illustration of a device 100 for safe storing and expelling of a liquid solution, according to some embodiments of the invention.

Figure 1B:
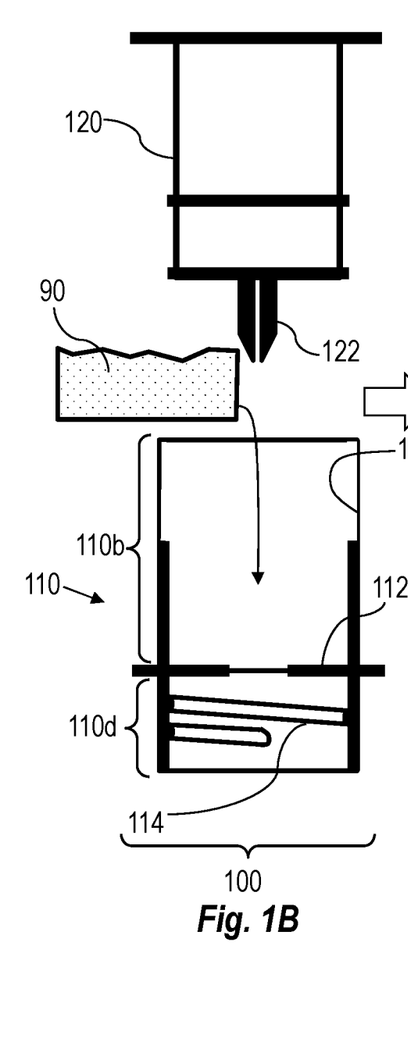
FIGS. 1B, 1C and 1D schematically show a process of prefilling of the device with a liquid solution, according to some embodiments of the invention.
Figure 1C:
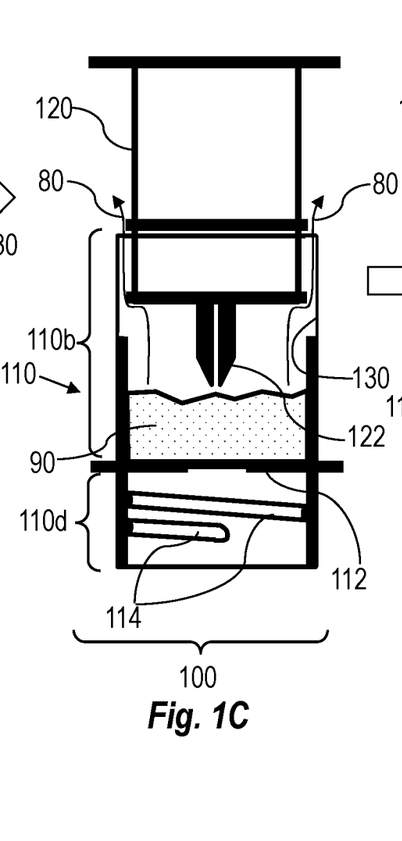
Figure 1D:
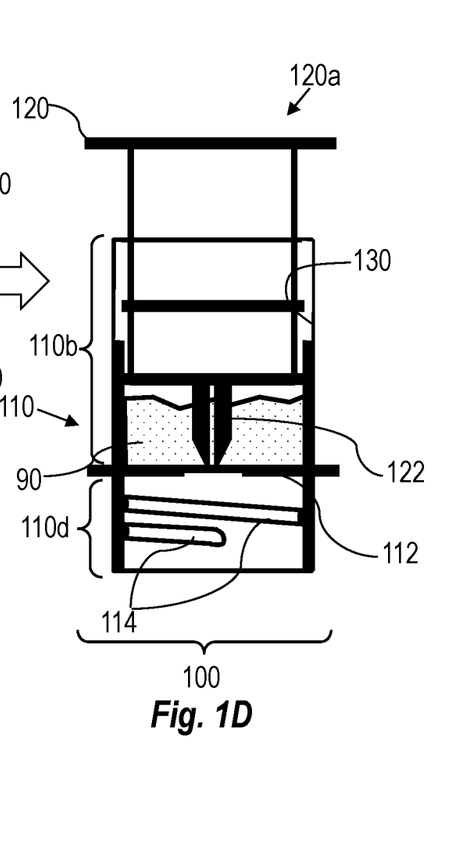

Reference is also made to FIGS. 1B, 1C and 1D, which schematically show a process of prefilling of device 100 with a liquid solution 90, according to some embodiments of the invention.

Figure 1E:
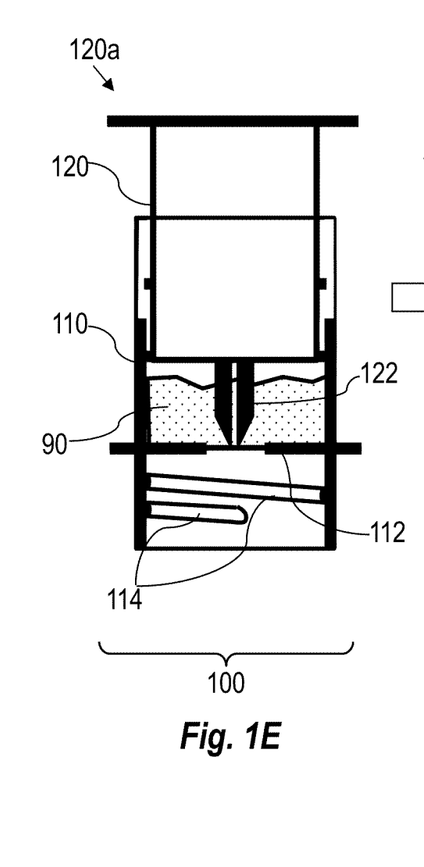
FIGS. 1E, 1F and 1G schematically show a process of expelling the liquid solution from the device, according to some embodiments of the invention.
Figure 1F:
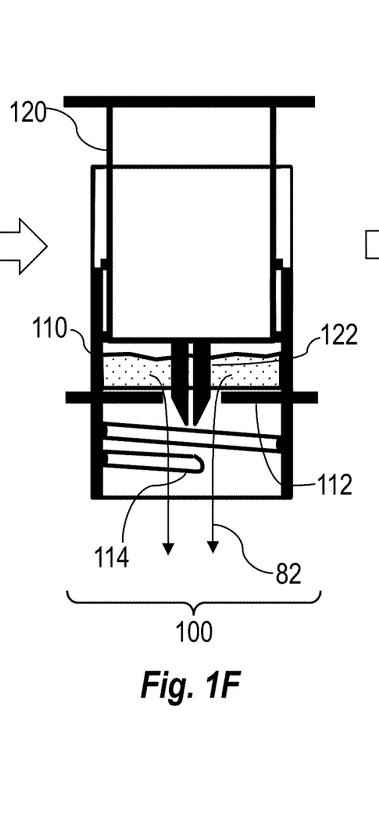
Figure 1G:
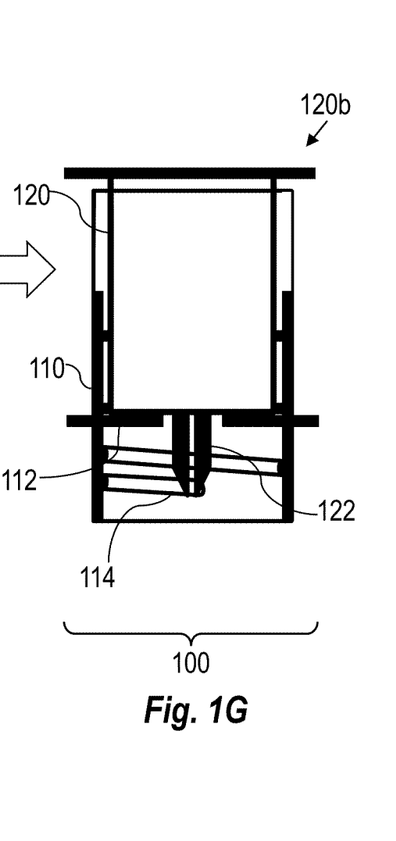

Reference is also made to FIGS. 1E, 1F and 1G, which schematically show a process of expelling of liquid solution 90 from device 100, according to some embodiments of the invention.

According to some embodiments of the invention, device 100 may include an annular body 110 and a piston 120.

Annular body 110 may include a proximal end 110a, a proximal portion 110b, a distal end 110c and a distal portion 110d. Annular body 110 may include a transverse member 112 between proximal portion 110b and distal portion 110d thereof. Transverse member 112 may have a circular shape. Transverse member 112 may be connected along its circumference to an inner lateral surface 110e of annular body 110. In some embodiments, transverse member 112 may be formed as an integral part of inner lateral surface 110e of annular body 110.

Annular body 110 may be connectable at its distal end 110c to an open proximal end of a test tube. In some embodiments, distal portion 110d of annular body 110 may be screwable to a proximal portion of the test tube. Annular body 110 may include an internal thread 114 at its distal portion 110d configured to mate with an external thread at the proximal portion of the test tube.

Piston 120 may fit tightly within proximal portion 110b of annular body 110. Piston 120 may be movable within proximal portion 110b of annular body 110. Piston 120 may be movable within proximal portion 110b of annular body 110 in a longitudinal direction 110f of annular body 110 between proximal end 110a and transverse member 112 of annular body 110. In some embodiments, piston 120 may be rotatable about its longitudinal axis within proximal portion 110b of annular body 110.

Piston 120 may be liquid tight. In some embodiments, piston 120 may include, on its external lateral surface, one or more lateral protrusions 121 to create a seal at an interface between piston 120 and annular body 110.

Piston 120 may include one or more longitudinal members 122 longitudinally protruding from piston 120 into an interior of proximal portion 110b of annular body 110. Each of one or more longitudinal members 122 may include a sharp distal end 122a to cut transverse member 112 of annular body 110 when one or more longitudinal members 122 are pushed against transverse member 112. In some embodiments, one or more longitudinal members 122 may be made as an integral part of piston 120.

In some embodiments, transverse member 112 of annular body 110 may include a thinned portion 112a. Thinned portion 112a of transverse member 112 of annular body 110 may facilitate cutting of transverse member 112 by longitudinal members 122 of piston 120.

A part of proximal portion 110b of annular body 110 may be prefilled with a liquid solution 90 (e.g., such as lysis buffer solution) and sealed with piston 120 (e.g., as shown in FIGS. 1B, 1C and 1D). For example, upon filling a part of proximal portion 110b of annular body 110 with liquid solution 90, piston 120 may be inserted into proximal portion 110b of annular body 110 up to an initial, non-actuated piston position 120a (e.g., as shown in FIG. 1D). Since piston 120 is liquid tight, liquid solution 90 may be safely stored within proximal portion 110b in a volume defined by inner lateral surface 110e and transverse member 112 of annular body 110, and piston 120.

In some embodiments, device 100 may be configured to cause at least a part of the air contained within proximal portion 110b of annular body 110 to escape therefrom when piston 120 is inserted into proximal portion 110b of annular body 110. For example, device 100 may be configured to cause at least a part of the air contained within proximal portion 110b of annular body 110 to escape therefrom when piston 120 is inserted into proximal portion 110b of annular body 110 up to initial, non-actuated piston position 120a.

In some embodiments, annular body 110 may include one or more longitudinal grooves 130 on inner lateral surface 110e of annular body 110. One or more longitudinal grooves 130 may longitudinally extend from proximal end 110a of annular body 110 along a part of proximal portion 110b of annular body 110. When piston 120 is being inserted into proximal portion 110b of annular body 110, e.g., up to initial, non-actuated piston position 120a, at least a part of the air contained within proximal portion 110b of annular body 110 may escape from proximal portion 110b of annular body 110 through one or more longitudinal grooves 130 (e.g., as schematically indicated by arrows 80 in FIG. 1C).

It is noted that other configurations of air escape means are also possible. Some of examples of air escape means are described below with respect to FIGS. 1O, 1P and FIGS. 1R, 1S, 1T.

Causing at least a part of the air contained within proximal portion 110b of annular body 110 to escape therefrom when piston 120 is being inserted into proximal portion 110b of annular body 110 may reduce air pressure within proximal portion 110b of annular body 110. Reduction of air pressure within proximal portion 110b of annular body 110 may, for example, enable the insertion of piston 120 to proximal portion 110b of annular body 110. High air pressure within proximal portion 110b of annular body 110 may cause liquid solution 90 to leak. Thus, reduction of air pressure within proximal portion 110b of annular body 110 may, for example, enhance safe storage of liquid solution 90 within proximal portion 110b of annular body 110.

Upon connection of annular body 110 to a test tube, piston 120 may be moved with respect to annular body 110 towards transverse member 112 of annular body 110 so as to cut transverse member 112 and to expel liquid solution 90 from proximal portion 110b of annular body 110 into the test tube (e.g., as schematically indicated by arrows 82 in FIG. 1F). Piston 120 may be moved, with respect to annular body 110, up to a final, actuated piston position 120b so as to expel all the liquid solution 90 from proximal portion 110b of annular body 110. Since piston 120 is liquid tight, piston 120 may prevent outflow of liquid solution 90 (and optionally other liquids that may be contained within the test tube) from the test tube as long as annular body 110 of device 100 is connected to the test tube (e.g., as shown in FIG. 1G).

As long as device 100 is connected to the test tube, the test tube with liquid solution 90 and the obtained sample may be safely delivered to, for example, a laboratory facility. During the delivery, liquid solution 90 may interact with the obtained sample so that the obtained sample may be ready for further analysis immediately with its arrival at the laboratory facility.

In some embodiments, device 100 may be configured to releasably lock piston 120 with respect to annular body 110 to prevent unintended movement of piston 120 with respect to annular body 110.

In some embodiments, device 100 may be configured to releasably lock piston 120 in its initial, non-actuated piston position 120a. Releasably locking piston 120 in its initial, non-actuated piston position 120a may prevent unintended escape of piston 120 from within proximal portion 110b of annular body 110 and may prevent unintended cutting of transverse member 112 of annular body 110 by one or more longitudinal members 122 of piston 120. This may, for example, ensure safe storage of liquid solution 90 within device 100.

In various embodiments, device 100 may be configured to lock, or releasably lock, piston 120 in its final, actuated piston position 120b. Locking piston 120 in its final, actuated piston position 120b may, for example, ensure that liquid solution 90 (and other liquids optionally contained within the test tube) does not escape from the test tube as long as device 100 is connected to the test tube. This may, for example, ensure safe delivery/transportation of the test tube containing liquid solution 90.

Some example of safety lock means of piston 120 with respect to annular body 110 are shown below with respect to FIGS. 1H, 1I, 1J and FIGS. 1K, 1L, 1M, 1N. It is noted that other configurations are also possible.

Figure 1H:
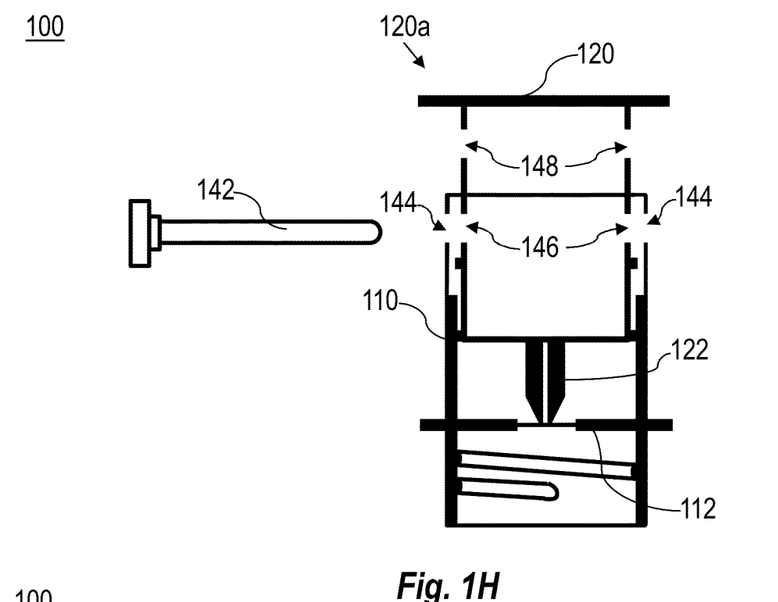
FIGS. 1H, 1I and 1J are schematic illustrations of the device for safe storing and expelling of a liquid solution, including a piston lock pin to releasably lock a piston with respect to an annular body of the device, according to some embodiments of the invention.
Figure 1I:
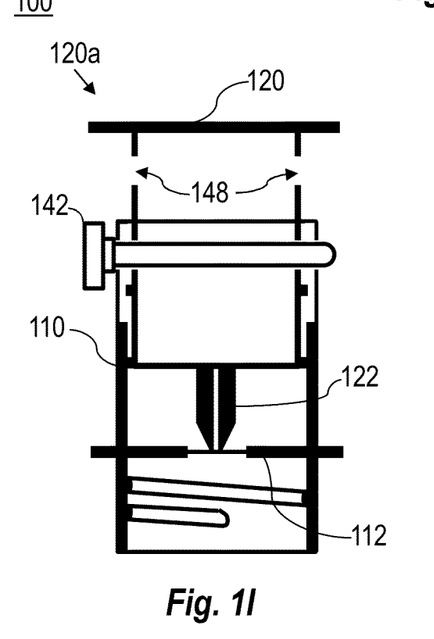
Figure 1J:
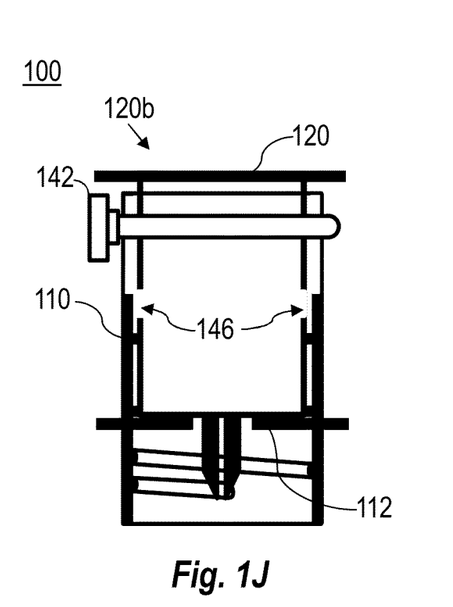

Reference is now made to FIGS. 1H, 1I and 1J, which are schematic illustrations of a device 100 for safe storing and expelling of a liquid solution, including a piston lock pin 142 to releasably lock piston 120 with respect to annular body 110 of device 100, according to some embodiments of the invention.

In some embodiments, device 100 may include a piston lock pin 142. In some embodiments, piston lock pin 142 may releasably lock piston 120 with respect to annular body 110 in initial, non-actuated piston position 120a (e.g., as shown in FIG. 1I). For example, annular body 110 may include a pair of opposite holes 144 and piston 120 may include a first pair of opposite holes 146. Holes 144, 146 may be shaped, sized and positioned to tightly and releasably receive piston lock pin 142 therein in order to lock piston 120 with respect to annular body 110 in its initial, non-actuated piston position 120a.

In some embodiments, piston lock pin 142 may releasably lock piston 120 with respect to annular body 110 in its final, actuated piston position 120b (e.g., as shown in FIG. 1J). For example, piston 120 may include a second pair of opposite holes 148. Holes 148 may be shaped, sized and positioned such that, when piston lock pin 142 is releasably received within holes 144 of annular body 110 and holes 148 of piston 120, piston lock pin 142 locks piston 120 with respect to annular body 110 in final, actuated piston position 120b.

Reference is now made to FIGS. 1K, 1L, 1M and 1N, which are schematic illustrations of a device 100 for safe storing and expelling of a liquid solution, capable of releasably locking piston 120 with respect to annular body 110 of device 100, according to some embodiments of the invention.

Figure 1K:
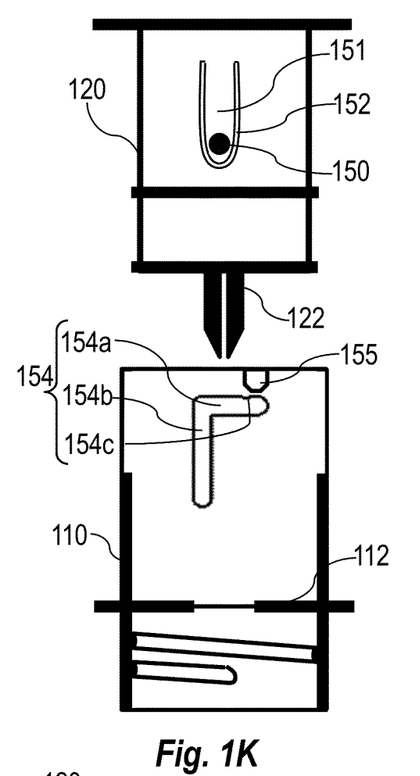
FIGS. 1K, 1L, 1M and 1N are schematic illustrations of the device for safe storing and expelling of a liquid solution, capable of releasably locking the piston with respect to the annular body of the device, according to some embodiments of the invention.

In some embodiments, piston 120 may include a locking protrusion 150 on its lateral surface. In some embodiments, piston 120 may include a longitudinal lateral resilient portion 151 on its lateral surface. In some embodiments, locking protrusion 150 may be connected to longitudinal lateral resilient portion 151 of the lateral surface of piston 120. For example, a substantially U-shaped cut 152 may be made on the lateral surface of piston 120 to form longitudinal lateral resilient portion 151.

In various embodiments, annular body 110 may include a locking cut 154 on a lateral surface of proximal portion 110b of annular body 110. Locking cut 154 may include a circumferential portion 154a extending along a part of a circumference of proximal portion 110b of annular body 110. Locking cut 154 may include a longitudinal portion 154b connected to circumferential portion 154a and longitudinally extending along a part of a length of proximal portion 110b of annular body 110.

In some embodiments, annular body 110 may include, at its proximal end 110a, a locking protrusion entry location 155. Locking protrusion entry location 155 may enable insertion of locking protrusion 150 of piston 120 into circumferential portion 154a of locking cut 154. In some embodiments, locking protrusion entry location 155 may include a sloped portion on inner lateral surface 110e at proximal end 110a of annular body 110.

Figure 1L:
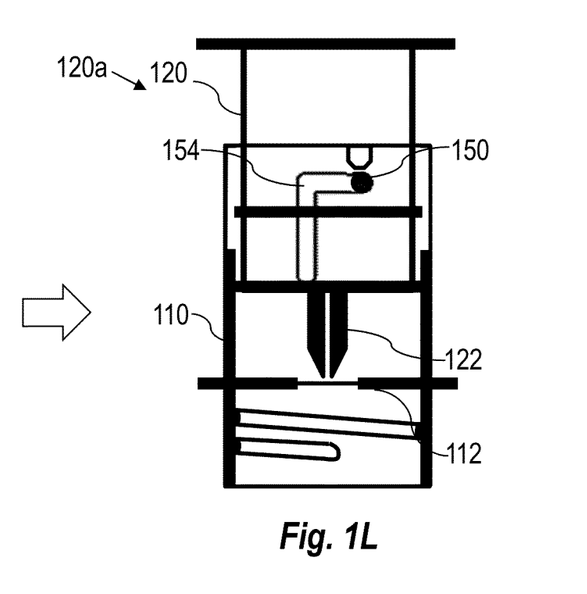

When piston 120 is inserted into proximal portion 110b of annular body 110, locking protrusion 150 may enter into circumferential portion 154a of locking cut 154 via locking protrusion entry location 155 of annular body 110. For example, the sloped portion of locking protrusion entry location 155 may push locking protrusion 150 connected to longitudinal lateral resilient portion 151 of piston 120 inwardly into piston 120 to let piston 120 be moved into annular body 110. When locking protrusion 150 reaches circumferential portion 154a of locking cut 154, longitudinal lateral resilient portion 151 of piston 120 may push locking protrusion 150 connected thereto outwardly from piston 120 into circumferential portion 154a of locking cut 154 (e.g., as shown in FIG. 1L). Circumferential portion 154a of locking cut 154 may include a stopper 154c to lock locking protrusion 150 within circumferential portion 154a of locking cut 154 to prevent rotation of piston 120 with respect to annular body 110 until a torque that exceeds a predefined torque value is applied on piston 120. In this manner, piston 120 may be locked with respect to annular body 110 in its initial, non-actuated piston position 120a. Stopper 154c may, for example, include one or more protrusions projecting into circumferential portion 154a of locking cut 154 from one or more edges of circumferential portion 154a of locking cut 154.

Figure 1M:
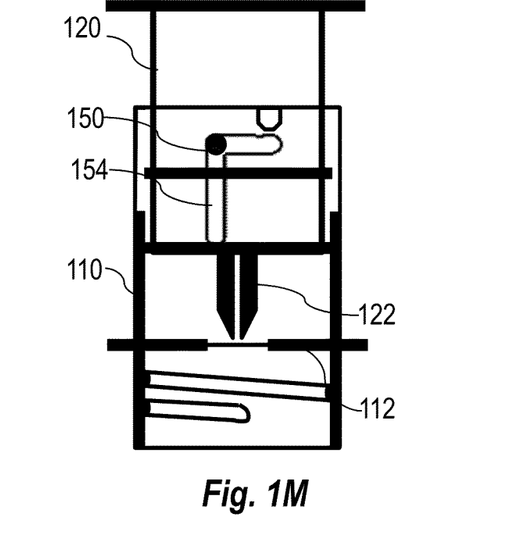
Figure 1N:
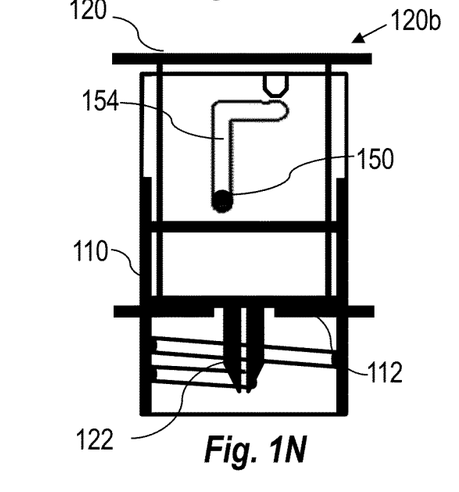

When a torque that exceeds the predefined torque value is applied on piston 120, piston 120 may be rotated with respect to annular body 110 until locking protrusion 150 movable within circumferential portion 154a of locking cut 154 reaches longitudinal portion 154b of locking cut 154 (e.g., as shown in FIG. 1M). Piston 120 may be then longitudinally pushed into annular body 110 until piston 120 reaches final, actuated piston position 120b while locking protrusion 150 may move within longitudinal portion 154b of locking cut 154 (e.g., as shown in FIG. 1N). In some embodiments, longitudinal portion 154b of locking cut 154 may include a stopper to lock locking protrusion 150 within longitudinal portion 154b of locking cut 154.

It is noted that other configurations of safety lock means of piston 120 with respect to annular body 110 are also possible. For example, annular body 110 may include a locking recess (not shown) on its inner lateral surface 110e, e.g., instead of locking cut 154. The locking recess may, for example, include one or more apertures on the lateral surface of annular body 110 to lock locking protrusion 150 of piston 120 in at least one of initial, non-actuated piston position 120a and final, actuated piston position 120b (e.g., instead of stoppers 154c). Locking protrusion entry location 155 may, for example, include an aperture, a recess or an indent extending from proximal end 110a of annular body 110 and connected with the circumferential portion of the locking cut or locking recess. Different combinations of the safety lock means components are also possible.

Figure 1O:
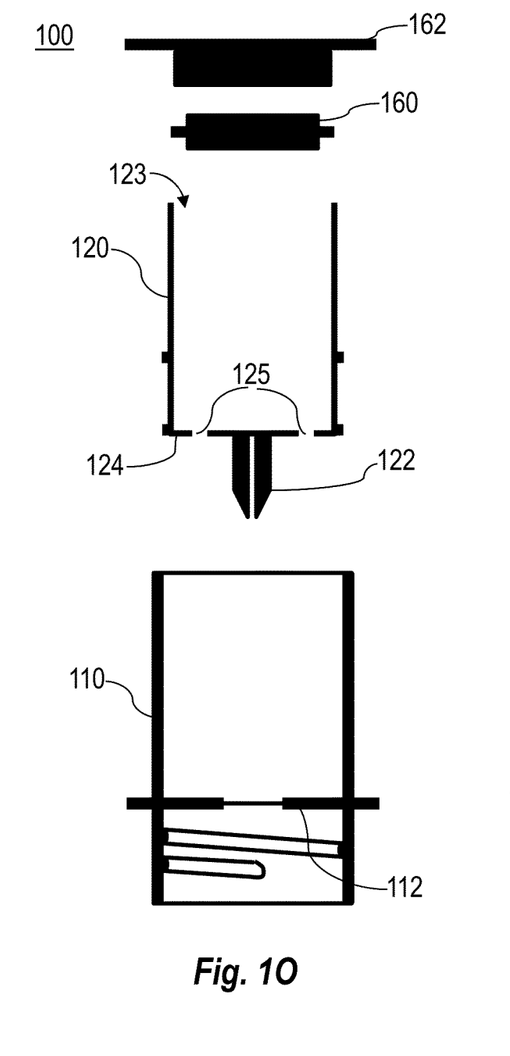
FIGS. 1O and 1P, which are schematic illustrations of a device for safe storing and expelling of a liquid solution, including a piston having one or more air escape apertures, according to some embodiments of the invention.
Figure 1P:
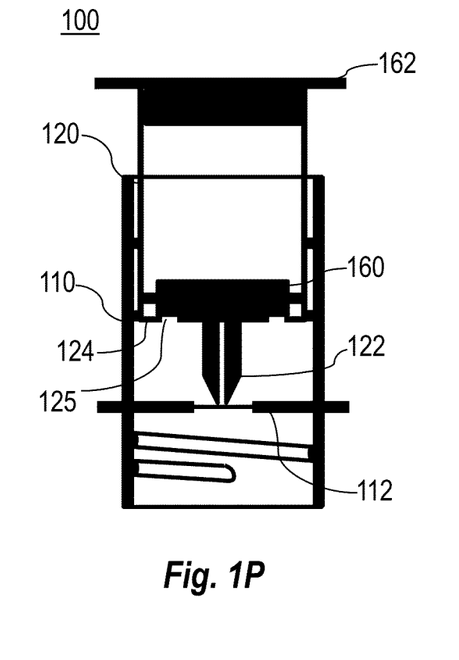

Reference is now made to FIGS. 1O and 1P, which are schematic illustrations of a device 100 for safe storing and expelling of a liquid solution, including a piston 120 having one or more air escape apertures, according to some embodiments of the invention.

In some embodiments, piston 120 may have a hollow cylindrical body having open proximal end 123 and a closed distal end 124. Longitudinal members 122 may protrude from closed distal end 124.

In some embodiments, piston 120 may include one or more air escape apertures 125 on closed distal end 124 of piston 120. When piston 120 is inserted into proximal portion 110b of annular body 110, e.g., up to initial, non-actuated piston position 120a, at least a part of the air contained within proximal portion 110b of annular body 110 may escape from proximal portion 110b of annular body 110 through one or more air escape apertures 125 on closed distal end 124 of piston 120.

In some embodiments, device 100 may include a liquid tight plug 160 fitting tightly within the cylindrical body of piston 120. Upon letting at least a portion of the air contained within proximal portion 110b of annular body 110 to escape from proximal portion 110b of annular body 110 through one or more air escape apertures 125 on closed distal end 124 of piston 120, plug 160 may be tightly received within the cylindrical body of piston 120 to prevent outflow of liquid solution 90 from proximal portion 110b of annular body 110 through one or more air escape apertures 125.

In some embodiments, device 100 may include a cover 162 to cover open proximal end 123 of piston 120.

Figure 1R:
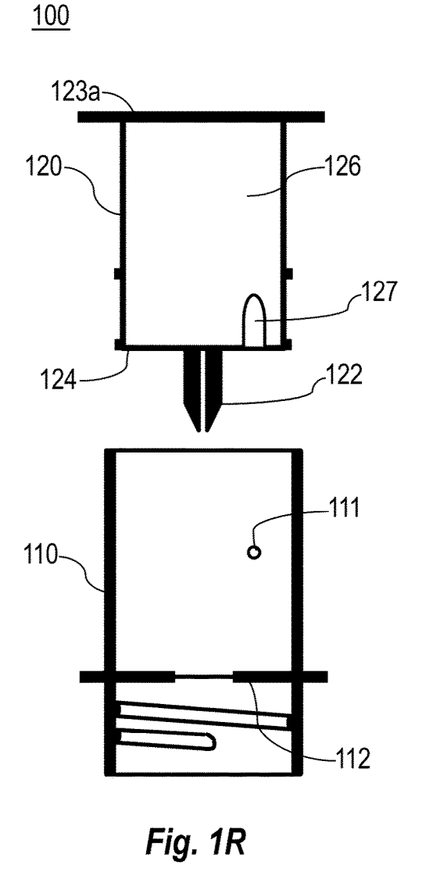
FIGS. 1R, 1S and 1T, which are schematic illustrations of a device for safe storing and expelling of a liquid solution, including a piston having an air escape slot, according to some embodiments of the invention.
Figure 1S:
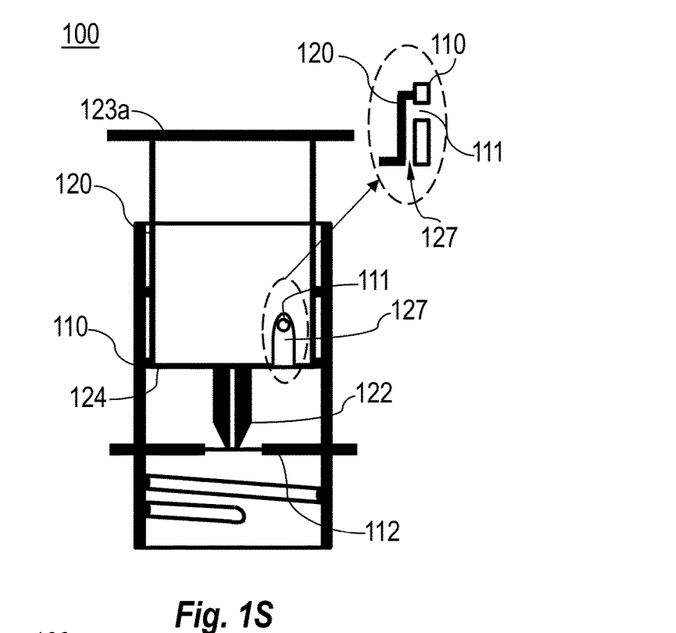
Figure 1T:
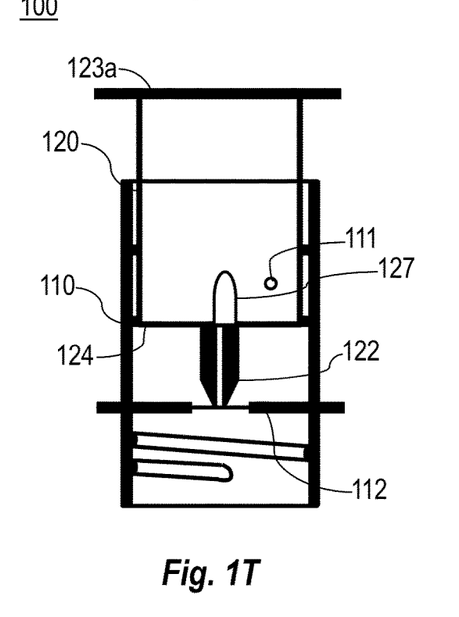

Reference is now made to FIGS. 1R, 1S and 1T, which are schematic illustrations of a device 100 for safe storing and expelling of a liquid solution, including a piston 120 having an air escape slot, according to some embodiments of the invention.

In some embodiments, piston 120 may have a cylindrical body having a proximal end 123a and distal end 124. In some embodiments, piston 120 may include an air escape slot 127 on its external lateral surface 126 at its distal end 124. In some embodiments, annular body 110 may include an air escape aperture 111 on the lateral surface of proximal portion 110b of annular body 110.

When piston 120 is inserted into proximal portion 110b of annular body 110, e.g., up to initial, non-actuated piston position 120a, a fluid communication between air escape slot 127 of piston 120 and air escape aperture 111 of annular body 110 may be formed, and at least a part of the air contained within proximal portion 110b of annular body 110 may escape from proximal portion 110b of annular body 110 through air escape slot 127 of piston 120 and air escape aperture 111 of annular body 110.

Upon letting at least a portion of the air contained within proximal portion 110b of annular body 110 to escape from proximal portion 110b of annular body 110 through air escape slot 127 of piston 120 and air escape aperture 111 of annular body 110, air escape slot 127 of piston 120 and air escape aperture 111 of annular body 110 may be fluidically disconnected, for example by rotating piston 120 with respect to annular body 110, to seal proximal portion 110b of annular body 110 by piston 120.

Reference is now made to FIGS. 2A, 2B, 2C and 2D, which are 3D diagrams of a device 200 for safe storing and expelling of a liquid solution, according to some embodiments of the invention.

Figure 2A:
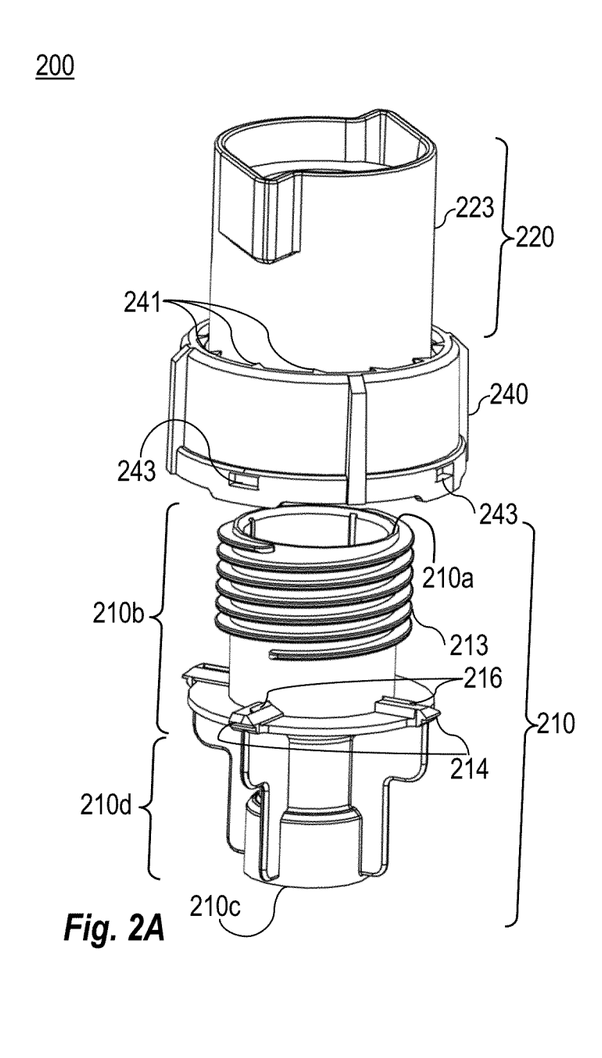
FIGS. 2A, 2B, 2C and 2D are 3D diagrams of the device for safe storing and expelling of a liquid solution, according to some embodiments of the invention.
Figure 2B:
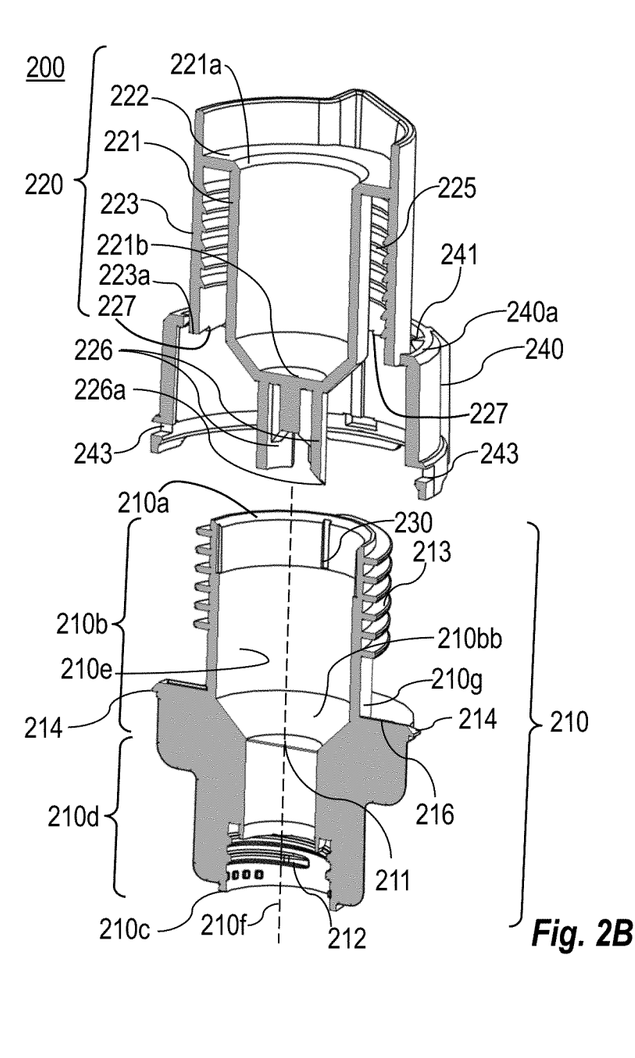
Figure 2C:
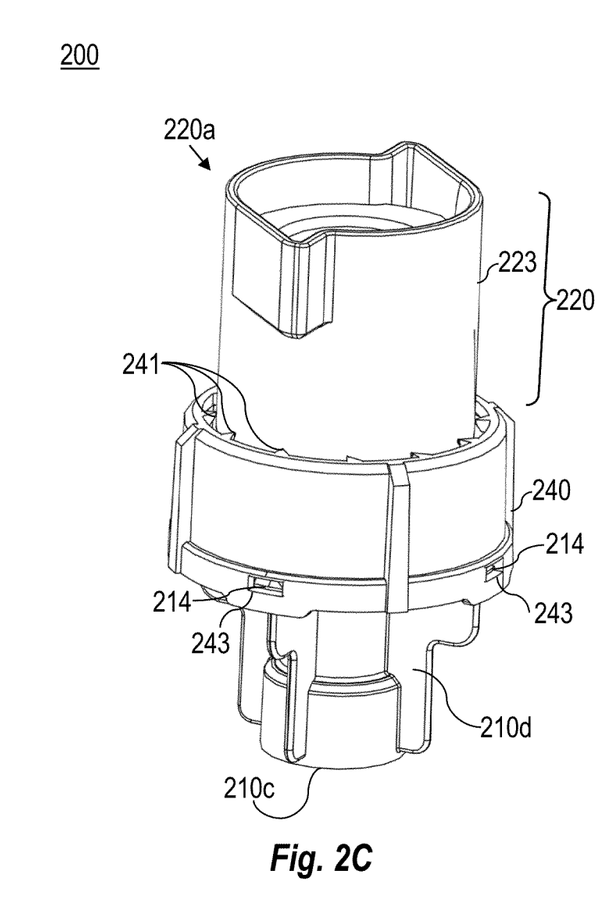
Figure 2D:
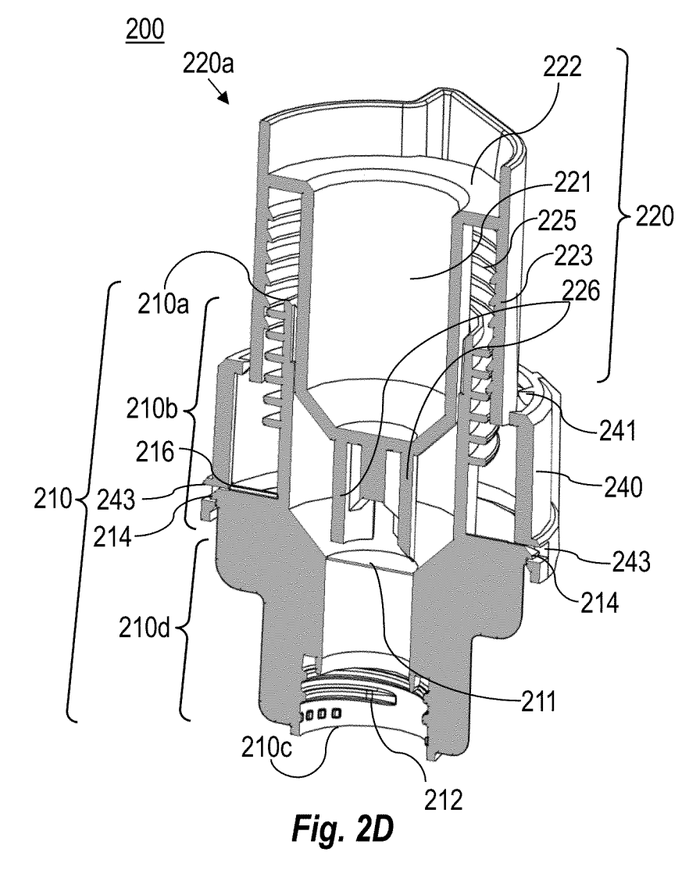

FIGS. 2A and 2B show disassembled device 200, and FIGS. 2C and 2D show assembled device 200. FIGS. 2A and 2C show perspective views of device 200, and FIGS. 2B and 2D show perspective section views of device 200.

According to some embodiments of the invention, device 200 may include an annular body 210 and a piston 220.

Annular body 210 may include a proximal end 210a, a proximal portion 210b, a distal end 210c and a distal portion 210d. Annular body 210 may include a transverse member 211 between proximal portion 210b and distal portion 210d thereof. Transverse member 211 may have a circular shape. Transverse member 211 may be connected along its circumference to an inner lateral surface 210e of annular body 210. In some embodiments, transverse member 211 may be formed as an integral part of inner lateral surface 210e of annular body 210.

Annular body 210 may be connectable at its distal end 210c to an open proximal end of a test tube. In some embodiments, distal portion 210d of annular body 210 may be screwable to a proximal portion of the test tube. Annular body 210 may include an internal thread 212 at its distal portion 210d mating with an external thread at the proximal portion of the test tube.

In some embodiments, piston 220 may include: a first annular piston body 221 fitting tightly within proximal portion 210b of annular body 210; a transverse piston portion 222 projecting outwardly from a proximal end 221a of first annular piston body 221; and a second annular piston body 223 connected to transverse piston portion 222 and surrounding first annular piston body 221 such that a gap 224 is formed between first annular piston body 221 and second annular piston body 223. Gap 224 may receive at least a part of proximal portion 210b of annular body 210. First annular piston body 221 may be liquid tight.

In some embodiments, first annular piston body 221 may include, at its external lateral surface, one or more lateral protrusions (e.g., like one or more lateral protrusions 121 described above with respect to FIG. 1A) to create a seal at an interface between first annular piston body 221 and annular body 210.

In some embodiments, piston 220 may be screwable to proximal portion 210b of annular body 210. In some embodiments, annular body 210 may include an external thread 213 on its proximal portion 210b, and second annular piston body 223 may include an internal thread 225 configured to mate with external thread 213 of annular body 210.

Piston 220 may include one or more longitudinal members 226 longitudinally protruding from closed distal end 221b of first annular piston body 221 into an interior of proximal portion 210b of annular body 210. Each of one or more longitudinal members 226 may include a sharp distal end 226a configured to cut transverse member 211 of annular body 210 when one or more longitudinal members 226 are pushed against transverse member 211. For example, when piston 220 is screwed to proximal portion 210b of annular body 210, longitudinal members 226 may cut transverse member 211 along at least a portion of the circumference thereof. In some embodiments, one or more longitudinal members 226 may be made as an integral part of closed distal end 221b of first annular piston body 221.

A part of proximal portion 210b of annular body 210 may be prefilled with a liquid solution (e.g., such as lysis buffer solution), and piston 220 may be screwed to proximal portion 210b of annular body 210 so as to seal proximal portion 210b of annular body 210 with first annular piston body 221. Since first annular piston body 221 is liquid-tight, the liquid solution may be safely stored in a volume defined by inner lateral surface 210e of annular body 210, transverse member 211 of annular body 210, and first annular piston body 221 of piston 220.

In some embodiments, annular body 210 may include one or more longitudinal grooves 230 on its inner lateral surface 210e. One or more longitudinal grooves 230 may longitudinally extend from proximal end 210a of annular body 210 along a part of proximal portion 210b annular body 210. When piston 220 is screwed to proximal portion 210b of annular body 210, for example up to its initial, non-actuated piston position 220a, at least a part of the air contained within proximal portion 210b of annular body 210 may escape from proximal portion 210b of annular body 210 through one or more longitudinal grooves 230.

In some embodiments, at least a part 210bb of an interior of proximal portion 210b of annular body 210 may taper in a longitudinal direction 210f of annular body 210 extending between proximal end 210a and distal end 210c of annular body 210. Tapered part 210bb may, for example, enhance expelling of the liquid solution by piston 220 upon cutting of transverse member 211.

In some embodiments, device 200 may be configured to releasably lock piston 220 with respect to annular body 210 to prevent unintended screwing and unscrewing of piston 220 with respect to annular body 210.

In some embodiments, device 200 may be configured to releasably lock piston 220 with respect to annular body 210 in an initial, non-actuated piston position 220a.

In some embodiments, device 200 may include a piston locking annular body 240. Piston locking annular body 240 may lock piston 220 in its initial, non-actuated piston position 220a to prevent unintended screwing and unscrewing of piston 220 with respect to annular body 210.

Piston locking annular body 240 may be connected at its proximal end 240a to second annular piston body 223. In some embodiments, piston locking annular body 240 may be connected to second annular piston body 223 at multiple connection points 241. In some embodiments, piston locking annular body 240 may be made as an integral part of piston 220.

In some embodiments, piston locking annular body 240 may be connectable to annular body 210. In some embodiments, annular body 210 may include lateral protrusions 214 projecting outwardly from an external lateral surface 210*g* of annular body 210, and piston locking annular body 240 may include mating cuts 243 on its lateral surface (e.g., adjacent to its distal end 240*b*). Cuts 243 and lateral protrusions 214 may be shaped and sized to cause each of cuts 243 to receive and lock one of lateral protrusions 214 when piston locking annular body 240 is longitudinally pressed with respect to annular body 210 to thereby lock piston locking annular body 240, and piston 220 connected thereto, with respect to annular body 210.

In some embodiments, connection points 241 may be configured to withstand torque values that are below a predefined torque threshold and to break when subjected to torque values that exceed the predefined torque threshold. For example, if a torque applied on piston 220 is below the predefined torque threshold, piston 220 may remain connected to piston locking annular body 240 at connection points 241, and thus piston 220 may remain unmovable with respect to annular body 210 in its initial, non-actuated piston position 220*a*. This may prevent unintended unscrewing and screwing of piston 220 with respect to annular body 210. This may prevent unintended escape of piston 220 from proximal portion 210*b* of annular body 110 and unintended cutting of transverse member 211 of annular body 210 by one or more longitudinal members 226 of piston 220. This may, for example, ensure safe storage of the liquid solution within device 200. If the torque applied on piston 220 exceeds the predefined torque threshold, connection points 241 may break to let piston 220 be screwed to proximal portion 210*b* of annular body to cut transverse member 211 of annular body 210 with longitudinal members 226 of piston 220.

When device 200 containing the liquid solution is connected to the test tube, a torque that is greater than the predefined torque threshold may be applied to piston 220 to break connection points 241 between piston 220 and piston locking annular body 240. Piston 220 may be then screwed to proximal portion 210*b* of annular body 210 to cut transverse member 211 of annular body 210 with one or more longitudinal members 226 of piston 220 and to expel the liquid solution from proximal portion 210*b* of annular body 210 into the test tube. Piston 220 may be tightly screwed to proximal portion 210*b* of annular body 210 up to a final, actuated piston position 220*b* so as to close cut transverse member 211 of annular body 210 with closed distal end 221*b* of first annular piston body 221. Since first annular piston body 221 is liquid-tight, it may prevent outflow of the liquid solution (and optionally other liquids that may be contained within the test tube) from the test tube as long as device 200 is connected to the test tube.

In some embodiments, device 200 may be configured to lock piston 220 with respect to annular body 210 in its final, actuated piston position 220*b*. This may prevent unintended unscrewing of piston 220 from proximal portion 210*b* of piston 210 to ensure that no outflow of the liquid solution (and optionally other liquids that may be contained within the test tube) from the test tube occurs.

In some embodiments, second annular piston body 223 may include teeth 227 longitudinally protruding from a distal end 223*a* of second annular piston body 223, and annular body 210 may include one or more latches 216 configured to mate with teeth 227. In some embodiments, one or more latches 216 may project outwardly from external lateral surface 210*g* of annular body 210. When piston 220 is being tightly screwed to proximal portion 210*b* of annular body 210 up to its final, actuated piston position 220*b*, one or more latches 216 may engage with teeth 227 to prevent unscrewing of piston 220 from proximal portion 210*b* of annular body 210 and to lock piston 220 in its final, actuated piston position 220*b*.

Figure 3:
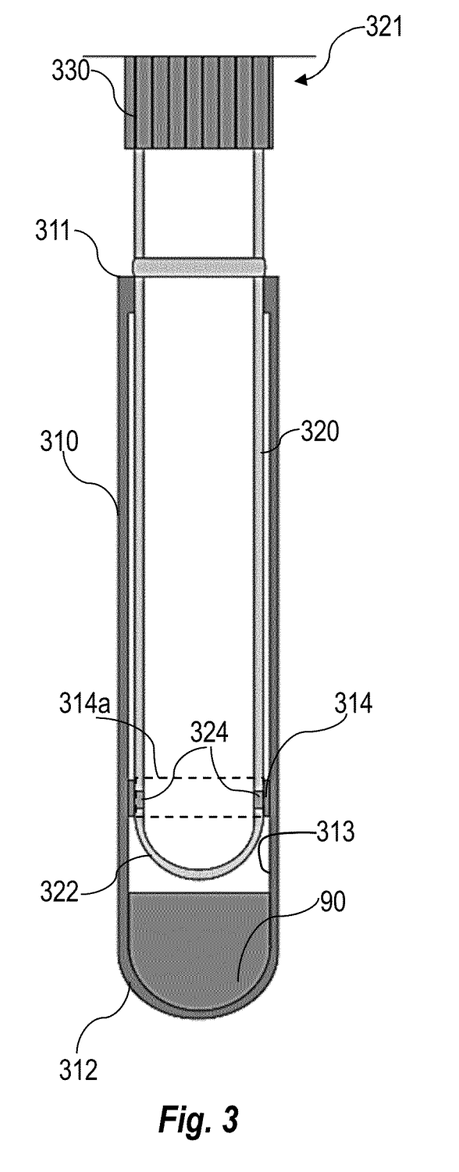
FIG. 3 is a schematic illustration of a device for safe storing and expelling of a liquid solution, including an external annular body and an internal annular body, according to some embodiments of the invention.

Reference is now made to FIG. 3, which is a schematic illustration of a device 300 for safe storing and expelling of a liquid solution, including an external annular body and an internal annular body, according to some embodiments of the invention.

According to some embodiments of the invention, device 300 may include an external annular body 310 and an inner annular body 320.

External annular body 310 may have an open proximal end 311 and a closed distal end 312. External annular body 310 may include a lateral protrusion 314 projecting inwardly from an inner lateral surface 313 of external annular body 310 into an interior of external annular body 310 along at least a portion of a circumference of external annular body 310. Lateral protrusion 314 may be in a distal portion of external annular body 310 (e.g., closer to distal end 312 rather than to proximal end 311 thereof). Lateral protrusion 314 may form a constriction region 314*a* within the interior of external annular body 310.

Inner annular body 320 may have an open proximal end 321 and a closed distal end 322. Inner annular body 320 may fit tightly within constriction region 314*a* in the interior of external annular body 310. Inner annular body 320 may include one or more apertures 324 on its lateral surface. Aperture(s) 324 may be in a distal portion of inner annular body 320 (e.g., closer to distal end 322 rather than to proximal end 321 thereof).

A part of the distal portion of external annular body 310 may be prefilled with liquid solution 90, and inner annular body 320 may be inserted into the interior of external annular body 310 such that one or more apertures 324 in inner annular body 320 are positioned within constriction region 314*a* of external annular body 310 and are sealed by lateral protrusion 314 thereof. When inner annular body 320 is inserted into the interior of external annular body 310, at least a part of the air contained within the interior of external annular body 310 may escape therefrom through one or more apertures 324 in inner annular body 320.

In some embodiments, device 300 may include a cap 330 to seal open proximal end 321 of inner annular body 320.

When a longitudinal force that exceeds a predetermined force threshold is applied on inner annular body 320, inner annular body 320 may move towards distal end 312 of external annular body 310, and liquid solution 90 may flow from external annular body 310 into an interior of inner annular body 320. Since external annular body 320 remains sealed by inner annular body positioned therein and inner annular body 320 is sealed by cap 330, no outflow of liquid solution 90 from device 300 occurs.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A device for safe storing and expelling of a liquid solution, the device comprising:
   an annular body having a proximal end, a proximal portion, a distal end and a distal portion and comprising a transverse member, the transverse member is connected along a circumference of the transverse member to an inner lateral surface of the annular body between the proximal portion and the distal portion of the annular body;
   a liquid-tight piston fitting tightly and movable within the proximal portion of the annular body,
      wherein the piston comprises one or more longitudinal members longitudinally protruding from the piston into an interior of the proximal portion of the annular body, wherein each of the one or more longitudinal members comprises a sharp end configured to cut the transverse member of the annular body when the one or more longitudinal members is pushed against the transverse member of the annular body, and
      wherein the piston further comprises:
      a first liquid-tight annular piston body fitting tightly and movable within the proximal portion of the annular body,
      a transverse piston portion projecting outwardly from a proximal end of the first annular piston body, and
      a second annular piston body connected to the transverse piston portion and surrounding the first annular piston body such that a gap is formed between the first annular piston body and the second annular piston body, wherein the gap is configured to receive at least a part of the proximal portion of the annular body; and
      a piston locking annular body connected to the second annular piston body and connectable to the annular body,
      wherein the annular body comprises lateral protrusions projecting outwardly from an external lateral surface of the annular body,
      wherein the piston locking annular body comprises mating cuts on a lateral surface of the piston locking annular body, and
      wherein the cuts and the lateral protrusions are shaped and sized to cause each of the cuts to receive and lock one of the lateral protrusions when the piston locking annular body is longitudinally pressed with respect to the annular body.

2. The device of claim 1, configured to store a liquid solution in a volume defined by the inner lateral surface of the annular body, the transverse member of the annular body, and the piston.

3. The device of claim 1, further comprising a liquid solution in a volume defined by the inner lateral surface of the annular body, the transverse member of the annular body, and the piston.

4. The device of claim 1, wherein the annular body is connectable at the distal end of the annular body to an open end of a test tube.

5. The device of claim 1, wherein the distal portion of the annular body is screwable to a proximal portion of a test tube.

6. The device of claim 1, configured to cause at least a part of air contained within the proximal portion of the annular body to escape from the proximal portion of the annular body when the piston is being inserted into the proximal portion of the annular body.

7. The device of claim 1, wherein the annular body comprises one or more longitudinal grooves on the inner lateral surface of the annular body, and wherein the one or more longitudinal grooves longitudinally extend from the proximal end of the annular body along a part of the proximal portion of the annular body.

8. The device of claim 1,
   wherein the piston is movable with respect to the annular body between an initial, non-actuated piston position and a final, actuated piston position; and
   wherein the piston is releasably lockable with respect to the annular body in the initial, non-actuated piston position.

9. The device of claim 8, wherein the piston is one of lockable and releasably lockable with respect to the annular body in the final, actuated piston position.

10. The device of claim 1, wherein the piston is screwable to the proximal portion of the annular body, wherein the proximal portion of the annular body comprises an external thread, and wherein the second annular piston body comprises an internal thread configured to mate with the external thread of the proximal portion of the annular body.

11. The device of claim 1, wherein the piston locking annular body is connected to the second annular piston body at multiple connection points configured to withstand torque values that are below a predefined torque threshold and configured to break when subjected to torque values that exceed the predefined torque threshold.

12. The device of claim 1,
   wherein the second annular piston body comprises teeth longitudinally protruding from a distal end of the second annular piston body;
   wherein the annular body comprises one or more latches mating with teeth; and
   wherein the one or more latches are engageable with the teeth when the piston is tightly screwed to the proximal portion of the annular body to prevent unscrewing of the piston from the proximal portion of the annular body.

13. The device of claim 12, wherein the one or more latches project outwardly from an external lateral surface of the annular body.

\* \* \* \* \*